(12) United States Patent
Legler et al.

(10) Patent No.: US 11,986,534 B1
(45) Date of Patent: May 21, 2024

(54) TREATMENT OF ANTHRAX WITH PEGYLATED CAPSULE-DEGRADING ENZYME

(71) Applicant: The Government of the United States of America, as represented by the Secretary of the Navy, Arlington, VA (US)

(72) Inventors: Patricia M. Legler, Derwood, MD (US); Arthur M. Friedlander, Frederick, MD (US); Jaimee R. Compton, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 18/472,953

(22) Filed: Sep. 22, 2023

Related U.S. Application Data

(62) Division of application No. 17/577,893, filed on Jan. 18, 2022, now Pat. No. 11,786,601.

(60) Provisional application No. 63/140,455, filed on Jan. 22, 2021.

(51) Int. Cl.
*A61K 47/60* (2017.01)
*A61K 38/45* (2006.01)

(52) U.S. Cl.
CPC .............. *A61K 47/60* (2017.08); *A61K 38/45* (2013.01)

(58) Field of Classification Search
CPC ................................ A61K 47/60; A61K 38/45
See application file for complete search history.

(56) References Cited

PUBLICATIONS

Kocianova S, Vuong C, Yao Y, Voyich JM, Fischer ER, DeLeo FR, Otto M. Key role of poly-gamma-DL-glutamic acid in immune evasion and virulence of *Staphylococcus epidermidis*. J Clin Invest. Mar. 2005;115(3):688-94. doi: 10.1172/JCI23523. PMID: 15696197; PMCID: PMC546460. (Year: 2005).*

Scorpio A, Tobery SA, Ribot WJ, Friedlander AM. Treatment of experimental anthrax with recombinant capsule depolymerase. Antimicrob Agents Chemother. Mar. 2008;52(3):1014-20. doi: 10.1128/AAC.00741-07. Epub Dec. 26, 2007. PMID: 18160516; PMCID: PMC2258529. (Year: 2008).*

Wen, Zhensong and Jing-Ren Zhang. "Chapter 3—Bacterial Capsules." (2015). (Year: 2015).*

* cited by examiner

*Primary Examiner* — Louise W Humphrey
*Assistant Examiner* — John Paul Selwanes
(74) *Attorney, Agent, or Firm* — US Naval Research Laboratory; Roy Roberts

(57) ABSTRACT

A pegylated, circularly permuted construct of the CapD enzyme (a gamma glutamyl transferase enzyme acting as a hydrolase specific to poly-γ-D-glutamic acid) is used to treat anthrax and other bacterial infections, including but not limited to infection with strains that are resistant to available antibiotics.

5 Claims, 1 Drawing Sheet
Specification includes a Sequence Listing.

Survival of BALB/c mice against Ames

FIG. 1A

Survival of BALB/c mice against ΔAmes

FIG. 1B

SEQUENCE LISTING

```
Sequence total quantity: 5
SEQ ID NO: 1             moltype = AA  length = 528
FEATURE                  Location/Qualifiers
source                   1..528
                         mol_type = protein
                         organism = Bacillus anthracis
SEQUENCE: 1
MNSFKWGKKI ILFCLIVSLM GGIGVSCSFN KIKDSVKQKI DSMGDKGTYG VSASHPLAVE   60
EGMKVLKNGG SAVDAAIVVS YVLGVVELHA SGIGGGGGML IISKDKETFI DYRETTPYFT  120
GNQKPHIGVP GFVAGMEYIH DNYGSLPMGE LLQPAINYAE KGFKVDDSLT MRLDLAKPRI  180
YSDKLSIFYP NGEPIETGET LIQTDLARTL KKIQKEGAKG FYEGGVARAI SKTAKISLED  240
IKGYKVEVRK PVKGNYMGYD VYTAPPPFSG VTLLQMLKLA EKKEVYKDVD HTATYMSKME  300
EISRIAYQDR KKNLGDPNYV NMDPNKMVSD KYISTMKNEN GDALSEAEHE STTHFVIIDR  360
DGTVVSSTNT LSNFFGTGKY TAGFFLNNQL QNFGSEGFNS YEPGKRSRTF MAPTVLKKDG  420
ETIGIGSPGG NRIPQILTPI LDKYTHGKGS LQDIINEYRF TFEKNTAYTE IQLSSEVKNE  480
LSRKGLNVKK KVSPAFFGGV QALIKDERDN VITGAGDGRR NGTWKSNK               528

SEQ ID NO: 2             moltype = AA  length = 504
FEATURE                  Location/Qualifiers
REGION                   1..504
                         note = synthetic construct
source                   1..504
                         mol_type = protein
                         organism = synthetic construct
SEQUENCE: 2
MTTHFVIIDR DGTVVSSTNT LSNFFGTGKY TAGFFLNNQL QNFGSEGFNS YEPGKRSRTF   60
MAPTVLKKDG ETIGIGSPGG NRIPQILTPI LDKYTHGKGS LQDIINEYRF TFEKNTAYTE  120
IQLSSEVKNE LSRKGLNVKK KVSPAFFGGV QALIKDERDN VITGAGDGRR NGTWKSGGSG  180
TYGVSASHPL AVEEGMKVLK NGGSAVDAAI VVSYVLGVVE LHASGIGGGG GMLIISKDKE  240
TFIDYRETTP YFTGNQKPHI GVPGFVAGME YIHDNYGSLP MGELLQPAIN YAEKGFKVDD  300
SLTMRLDLAK PRIYSDKLSI FYPNGEPIET GETLIQTDLA RTLKKIQKEG AKGFYEGGVA  360
RAISKTAKIS LEDIKGYKVE VRKPVKGNYM GYDVYTAPPP FSGVTLLQML KLAEKKEVYK  420
DVDHTATYMS KMEEISRIAY QDRKKNLGDP NYVNMDPNKM VSDKYICTMK NENGDALSEA  480
EHESGSTENL YFQSGALEHH HHHH                                         504

SEQ ID NO: 3             moltype = AA  length = 499
FEATURE                  Location/Qualifiers
REGION                   1..499
                         note = synthetic construct
source                   1..499
                         mol_type = protein
                         organism = synthetic construct
SEQUENCE: 3
MTTHFVIIDR DGTVVSSTNT LSNFFGTGKY TAGFFLNNQL QNFGSEGFNS YEPGKRSRTF   60
MAPTVLKKDG ETIGIGSPGG NRIPQILTPI LDKYTHGKGS LQDIINEYRF TFEKNTAYTE  120
IQLSSEVKNE LSRKGLNVKK KVSPAFFGGV QALIKDERDN VITGAGDGRR NGTWKSGGSG  180
TYGVSASHPL AVEEGMKVLK NGGSAVDAAI VVSYVLGVVE LHASGIGGGG GMLIISKDKE  240
TFIDYRETTP YFTGNQKPHI GVPGFVAGME YIHDNYGSLP MGELLQPAIN YAEKGFKVDD  300
SLTMRLDLAK PRIYSDKLSI FYPNGEPIET GETLIQTDLA RTLKKIQKEG AKGFYEGGVA  360
```

-continued

```
RAISKTAKIS LEDIKGYKVE VRKPVKGNYM GYDVYTAPPP FSGVTLLQML KLAEKKEVYK  420
DVDHTATYMS KMEEISRIAY QDRKKNLGDP NYVNMDPNKM VSDKYICTMK NENGDALSEA  480
EHESIEGRVS LEHHHHHH                                                499

SEQ ID NO: 4            moltype = AA  length = 732
FEATURE                 Location/Qualifiers
REGION                  1..732
                        note = synthetic construct
source                  1..732
                        mol_type = protein
                        organism = synthetic construct
SEQUENCE: 4
MTTHFVIIDR DGTVVSSTNT LSNFFGTGKY TAGFFLNNQL QNFGSEGFNS YEPGKRSRTF  60
MAPTVLKKDG ETIGIGSPGG NRIPQILTPI LDKYTHGKGS LQDIINEYRF TFEKNTAYTE  120
IQLSSEVKNE LSRKGLNVKK KVSPAFFGGV QALIKDERDN VITGAGDGRR NGTWKSGGSG  180
TYGVSASHPL AVEEGMKVLK NGGSAVDAAI VVSYVLGVVE LHASGIGGGG GMLIISKDKE  240
TFIDYRETTP YFTGNQKPHI GVPGFVAGME YIHDNYGSLP MGELLQPAIN YAEKGFKVDD  300
SLTMRLDLAK PRIYSDKLSI FYPNGEPIET GETLIQTDLA RTLKKIQKEG AKGFYEGGVA  360
RAISKTAKIS LEDIKGYKVE VRKPVKGNYM GYDVYTAPPP FSGVTLLQML KLAEKKEVYK  420
DVDHTATYMS KMEEISRIAY QDRKKNLGDP NYVNMDPNKM VSDKYICTMK NENGDALSEA  480
EHESGSGAKK IVPRDCGCKP CICTVPEVSS VFIFPPKPKD VLTITLTPKV TCVVVDISKD  540
DPEVQFSWFV DDVEVHTAQT QPREEQFNST FRSVSELPIM HQDWLNGKEF KCRVNSAAFP  600
APIEKTISKT KGRPKAPQVY TIPPPKEQMA KDKVSLTCMI TDFFPEDITV EWQWNGQPAE  660
NYKNTQPIMD TDGSYFVYSK LNVQKSNWEA GNTFTCSVLH EGLHNHHTEK SLSHSPGKLG  720
IEGRLEHHHH HH                                                      732

SEQ ID NO: 5            moltype = AA  length = 736
FEATURE                 Location/Qualifiers
REGION                  1..736
                        note = synthetic construct
source                  1..736
                        mol_type = protein
                        organism = synthetic construct
SEQUENCE: 5
MTTHFVIIDR DGTVVSSTNT LSNFFGTGKY TAGFFLNNQL QNFGSEGFNS YEPGKRSRTF  60
MAPTVLKKDG ETIGIGSPGG NRIPQILTPI LDKYTHGKGS LQDIINEYRF TFEKNTAYTE  120
IQLSSEVKNE LSRKGLNVKK KVSPAFFGGV QALIKDERDN VITGAGDGRR NGTWKSGGSG  180
TYGVSASHPL AVEEGMKVLK NGGSAVDAAI VVSYVLGVVE LHASGIGGGG GMLIISKDKE  240
TFIDYRETTP YFTGNQKPHI GVPGFVAGME YIHDNYGSLP MGELLQPAIN YAEKGFKVDD  300
SLTMRLDLAK PRIYSDKLSI FYPNGEPIET GETLIQTDLA RTLKKIQKEG AKGFYEGGVA  360
RAISKTAKIS LEDIKGYKVE VRKPVKGNYM GYDVYTAPPP FSGVTLLQML KLAEKKEVYK  420
DVDHTATYMS KMEEISRIAY QDRKKNLGDP NYVNMDPNKM VSDKYICTMK NENGDALSEA  480
EHESGSGAKK IVPRDCGCKP CICTVPEVSS VFIFPPKPKD VLTITLTPKV TCVVVDISKD  540
DPEVQFSWFV DDVEVHTAQT QPREEQFNST FRSVSELPIM HQDWLNGKEF KCRVNSAAFP  600
APIEKTISKT KGRPKAPQVY TIPPPKEQMA KDKVSLTCMI TDFFPEDITV EWQWNGQPAE  660
NYKNTQPIMD TDGSYFVYSK LNVQKSNWEA GNTFTCSVLH EGLHNHHTEK SLSHSPGKLG  720
IEGRGSSGLE HHHHHH                                                  736
```

TREATMENT OF ANTHRAX WITH PEGYLATED CAPSULE-DEGRADING ENZYME

CROSS-REFERENCE TO RELATED APPLICATIONS

This Application is a division of U.S. patent application Ser. No. 17/577,893 filed Jan. 18, 2022 and claims the benefit of U.S. Provisional Patent Application No. 63/140,455 filed on Jan. 22, 2021, each of which is incorporated herein by reference in its entirety.

INCORPORATION BY REFERENCE

This Application incorporates by reference the Sequence Listing XML file submitted herewith via the patent office electronic filing system having the file name "111475US3-sequences.xml" and created on Sep. 22, 2023 with a file size of 9,653 bytes.

BACKGROUND

*Bacillus anthracis*, the causative agent of anthrax, has been known to develop antibiotic resistance. However, the bacteria relies on a capsule of poly-γ-D-glutamic acid to shield the bacterium from killing by phagocytic cells (such as in a human host). This polymer is unique to bacteria and is not present in humans; it serves to shield the bacterium from phagocytic cells in a human host. The anti-phagocytic property of the capsule is the primary mechanism of immune cell evasion utilized by *B. anthracis* and is critical for virulence.

CapD is a gamma glutamyl transferase enzyme acting as a protease specific to poly-γ-D-glutamic acid. CapD is normally autocatalytic and forms a heterodimer consisting of 35 kDa and 15 kDa polypeptides. When added exogenously to encapsulated bacilli, the enzyme efficiently degrades the capsule, essentially removing it from the surface of the bacilli, allowing neutrophils to kill the unencapsulated bacteria.

A need exists for novel treatments effective against anthrax infection, particularly in the event of infection with strains that are resistant to available antibiotics.

BRIEF SUMMARY

In a first embodiment, a purified and isolated protein is a pegylated, circularly permuted construct of the CapD enzyme having activity against poly-γ-D-glutamic acid and/or poly-γ-DL-glutamic acid, and optionally further comprising a Fc domain fused thereto.

In another embodiment, a method of treating an infection of bacteria in a subject involves administering the purified and isolated protein of the first embodiment to the subject, wherein the bacteria has a capsule.

BRIEF DESCRIPTION OF THE DRAWINGS

FIGS. 1A and 1B show data on survival of mice exposed to *B. anthracis* spores and treated with of CapD-CP$^{S334C}$ or control.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

The concept of combatting anthrax with the native form of CapD enzyme was discussed in U.S. Patent Application Publication 2010/0226906. This native enzyme has SEQ ID NO: 1 which is as follows:

```
MNSFKWGKKIILFCLIVSLMGGIGVSCSFNKIKDS

VKQKIDSMGDKGTYGVSASHPLAVEEGMKVLKNGG

SAVDAAIVVSYVLGVVELHASGIGGGGMLIISKD

KETFIDYRETTPYFTGNQKPHIGVPGFVAGMEYIH

DNYGSLPMGELLQPAINYAEKGFKVDDSLTMRLDL

AKPRIYSDKLSIFYPNGEPIETGETLIQTDLARTL

KKIQKEGAKGFYEGGVARAISKTAKISLEDIKGYK

VEVRKPVKGNYMGYDVYTAPPPFSGVTLLQMLKLA

EKKEVYKDVDHTATYMSKMEEISRIAYQDRKKNLG

DPNYVNMDPNKMVSDKYISTMKNENGDALSEAEHE

STTHFVIIDRDGTVVSSTNTLSNFFGTGKYTAGFF

LNNQLQNFGSEGFNSYEPGKRSRTFMAPTVLKKDG

ETIGIGSPGGNRIPQILTPILDKYTHGKGSLQDII

NEYRFTFEKNTAYTEIQLSSEVKNELSRKGLNVKK

KVSPAFFGGVQALIKDERDNVITGAGDGRRNGTWK

SNK.
```

Described herein are modified versions of this native CapD enzyme that are especially suited to treat anthrax infection. Of particular value are forms of CapD having improved stability and/or improved activity.

The native, or wild-type, CapD is produced as a single polypeptide which autocatalytically cleaves itself to produce a new N-terminal residue. As previously described in *J. Biol. Chem.* Vol 286(37):32586-32592 (2011), the circularly permuted construct of CapD (CapD-CP) does not require this cleavage and also exhibits enhanced stability as compared to the wild-type.

Stability was further improved by functionalizing the enzyme with polyethylene glycol (PEG), termed pegylation. Such treatment may also desirably reduce immunogenicity of the enzyme.

Pegylation of enzymes often results in reduction of enzyme activity by hindering substrate binding. The present inventors found that the S334C mutation allowed pegylation while retaining activity. This CapD-CP$^{S334C}$ protein has SEQ ID NO: 2 which is as follows:

```
MTTHFVIIDRDGTVVSSTNTLSNFFGTGKYTAGFF
LNNQLQNFGSEGFNSYEPGKRSRTFMAPTVLKKDG
ETIGIGSPGGNRIPQILTPILDKYTHGKGSLQDII
NEYRFTFEKNTAYTEIQLSSEVKNELSRKGLNVKK
KVSPAFFGGVQALIKDERDNVITGAGDGRRNGTWK
SGGSGTYGVSASHPLAVEEGMKVLKNGGSAVDAAI
VVSYVLGVVELHASGIGGGGGMLIISKDKETFIDY
RETTPYFTGNQKPHIGVPGFVAGMEYIHDNYGSLP
MGELLQPAINYAEKGFKVDDSLTMRLDLAKPRIYS
DKLSIFYPNGEPIETGETLIQTDLARTLKKIQKEG
AKGFYEGGVARAISKTAKISLEDIKGYKVEVRKPV
KGNYMGYDVYTAPPPFSGVTLLQMLKLAEKKEVYK
DVDHTATYMSKMEEISRIAYQDRKKNLGDPNYVNM
DPNKMVSDKYICTMKNENGDALSEAEHESGSTENL
YFQSGALEHHHHHH.
```

As detailed below, this protein was very effective in treating anthrax in an animal model.

The above protein includes a C-terminal polyhistidine tag to assist purification. An additional protein was developed with a cleavage site for Factor Xa integrated immediately prior to the tag in order to allow for its removal. This CapDcp S334C Clone XAI has SEQ ID NO: 3 which is as follows:

```
MTTHFVIIDRDGTVVSSTNTLSNFFGTGKYTAGFF
LNNQLQNFGSEGFNSYEPGKRSRTFMAPTVLKKDG
ETIGIGSPGGNRIPQILTPILDKYTHGKGSLQDII
NEYRFTFEKNTAYTEIQLSSEVKNELSRKGLNVKK
KVSPAFFGGVQALIKDERDNVITGAGDGRRNGTWK
SGGSGTYGVSASHPLAVEEGMKVLKNGGSAVDAAI
VVSYVLGVVELHASGIGGGGGMLIISKDKETFIDY
RETTPYFTGNQKPHIGVPGFVAGMEYIHDNYGSLP
MGELLQPAINYAEKGFKVDDSLTMRLDLAKPRIYS
DKLSIFYPNGEPIETGETLIQTDLARTLKKIQKEG
AKGFYEGGVARAISKTAKISLEDIKGYKVEVRKPV
KGNYMGYDVYTAPPPFSGVTLLQMLKLAEKKEVYK
DVDHTATYMSKMEEISRIAYQDRKKNLGDPNYVNM
DPNKMVSDKYICTMKNENGDALSEAEHESIEGRVS
LEHHHHHH.
```

The fusion of the Fc domain of an antibody to a therapeutic enzyme or protein can improve the in vivo circulation time of the enzyme and potentially reduce the amount of enzyme needed for protection. These immunotherapeutics can be recycled via the neonatal Fc-receptor (FcRn) in adults. However, because they are endocytosed during recycling these proteins are exposed to a low-pH environment where they can irreversibly denature and lose their enzymatic activity. It was found that pegylation of CapD prevents irreversible acid-denaturation of the enzyme. The fusion of the Fc-domain also unexpectedly imparted acid stability.

In further embodiments, a fusion protein of the immunoglobulin Fc domain to the S334C CapD-CP was generated to generate a homodimeric pegylated immunotherapeutic. The fusion of the Fc-domain increases the half-life of the enzyme in vivo, and also enhances the avidity of the enzyme to its polymeric substrate and improve clearance of low levels of bacteria. One such protein is Fc-CapD-CP w/Factor Xa site CF2A having SEQ ID NO: 4 which is as follows:

```
MTTHFVIIDRDGTVVSSTNTLSNFFGTGKYTAGFF
LNNQLQNFGSEGFNSYEPGKRSRTFMAPTVLKKDG
ETIGIGSPGGNRIPQILTPILDKYTHGKGSLQDII
NEYRFTFEKNTAYTEIQLSSEVKNELSRKGLNVKK
KVSPAFFGGVQALIKDERDNVITGAGDGRRNGTWK
SGGSGTYGVSASHPLAVEEGMKVLKNGGSAVDAAI
VVSYVLGVVELHASGIGGGGGMLIISKDKETFIDY
RETTPYFTGNQKPHIGVPGFVAGMEYIHDNYGSLP
MGELLQPAINYAEKGFKVDDSLTMRLDLAKPRIYS
DKLSIFYPNGEPIETGETLIQTDLARTLKKIQKEG
AKGFYEGGVARAISKTAKISLEDIKGYKVEVRKPV
KGNYMGYDVYTAPPPFSGVTLLQMLKLAEKKEVYK
DVDHTATYMSKMEEISRIAYQDRKKNLGDPNYVNM
DPNKMVSDKYICTMKNENGDALSEAEHESGSGAKK
IVPRDCGCKPCICTVPEVSSVFIFPPKPKDVLTIT
LTPKVTCVVVDISKDDPEVQFSWFVDDVEVHTAQT
QPREEQFNSTFRSVSELPIMHQDWLNGKEFKCRVN
SAAFPAPIEKTISKTKGRPKAPQVYTIPPPKEQMA
KDKVSLTCMITDFFPEDITVEWQWNGQPAENYKNT
QPIMDTDGSYFVYSKLNVQKSNWEAGNTFTCSVLH
EGLHNHHTEKSLSHSPGKLGIEGRLEHHHHHH.
```

Another embodiment based on the above is termed LCF7 and produced higher yields than the CF2A variant which was prone to aggregation. This LCF7 protein has SEQ ID NO: 5 which is as follows:

```
MTTHFVIIDRDGTVVSSTNTLSNFFGTGKYTAGFF
LNNQLQNFGSEGFNSYEPGKRSRTFMAPTVLKKDG
ETIGIGSPGGNRIPQILTPILDKYTHGKGSLQDII
NEYRFTFEKNTAYTEIQLSSEVKNELSRKGLNVKK
KVSPAFFGGVQALIKDERDNVITGAGDGRRNGTWK
```

-continued

```
SGGSGTYGVSASHPLAVEEGMKVLKNGGSAVDAAI

VVSYVLGVVELHASGIGGGGGMLIISKDKETFIDY

RETTPYFTGNQKPHIGVPGFVAGMEYIHDNYGSLP

MGELLQPAINYAEKGFKVDDSLTMRLDLAKPRIYS

DKLSIFYPNGEPIETGETLIQTDLARTLKKIQKEG

AKGFYEGGVARAISKTAKISLEDIKGYKVEVRKPV

KGNYMGYDVYTAPPPFSGVTLLQMLKLAEKKEVYK

DVDHTATYMSKMEEISRIAYQDRKKNLGDPNYVNM

DPNKMVSDKYICTMKNENGDALSEAEHESGSGAKK

IVPRDCGCKPCICTVPEVSSVFIFPPKPKDVLTIT

LTPKVTCVVVDISKDDPEVQFSWFVDDVEVHTAQT

QPREEQFNSTFRSVSELPIMHQDWLNGKEFKCRVN

SAAFPAPIEKTISKTKGRPKAPQVYTIPPPKEQMA

KDKVSLTCMITDFFPEDITVEWQWNGQPAENYKNT

QPIMDTDGSYFVYSKLNVQKSNWEAGNTFTCSVLH

EGLHNHHTEKSLSHSPGKLGIEGRGSSGLEHHHHH

H.
```

Fc-fusions are homodimeric and the poly-D-glutamate (PDGA) substrate is polymeric and anchored to the surface of the bacterial peptidoglycan. Avidity will affect the association rate of a homodimeric enzyme to its substrate, i.e., once one enzyme binds to the PDGA polymer, the second enzyme will bind more quickly. Thus, the increased avidity of the CapD Fc-fusion enhances the clearance of very low levels of bacteria in the blood.

EXAMPLES

Proteins were produced in *E. coli* and purified using standard techniques. In the case of pegylated proteins, pegylation was performed using (methyl-$PEG_{12}$)$_3$-$PEG_4$-maleimide with a molecular weight of 2360.75 g/mol or with PEG-maleimide with a molecular weight of ~2000 g/mol prior to purification.

Mice were exposed to five times the $LD_{50}$ of *B. anthracis* Ames spores and then treated by intraperitoneal injection of 40 mg/kg of CapD-CP$^{S334C}$ delivered 24 hours post-exposure every 8 hours for 2 days (for a total of six injections), or control injections of bovine serum albumin (BSA). The pegylated protein was protective in vivo against 5× $LD_{50}$ of *B. anthracis* Ames spore challenge (80% survival) as seen in FIG. 1A. Similar results were seen in mice exposed to the ΔAmes variant of anthrax as shown in FIG. 1B.

Further Embodiments

The depolymerases described herein can be produced in hosts besides *E. coli*. Pegylation can be done at sites other than those described and various forms of PEG-maleimides can be employed, for example single chain and branched chain forms, and those having different lengths.

It is contemplated that delivery of the enzyme to a subject known or suspected of having an anthrax infection, or of having been exposed to anthrax, might be effective to ameliorate the disease. Thus, a medicament is contemplated comprising the enzyme in conjunction with a pharmaceutically-acceptable carrier. In further embodiments, treatment includes providing not just the enzyme but one or more antibiotics.

The capsule depolymerases fused to Fc-domains described herein can be used to treat *Bacillus anthracis* (anthrax), *Staphylococcus epidermidis*, and other illnesses involving bacterial organisms having a capsule, including preferably those having a capsule which in part or in whole contains poly-γ-D-glutamic acid or mixed polymers of poly-γ-D/L-glutamic acid. Other types of capsule depolymerases, besides CapD, and including pegylated and/or Fc fusion forms of such enzymes, might be used on similarly against bacterial having capsules comprising substrates of these depolymerases.

In some preferable embodiments, the above-noted bacteria comprise, consist of, consist essentially of, or are, antibiotic resistant strains. Without wishing to be bound to a particular theory, it is believed that the capsule depolymerases fused to Fc-domains can remove the capsule from the bacterial surface making the bacterium susceptible to or more susceptible to killing by immune cells. Accordingly, the treatment is useful for a variety of illnesses caused by bacterial infections, including by way of illustration, but not limitation, septicemia and infections of deep tissue and prosthetic devices.

Administration of the therapy could be performed orally or parenterally, or intravenously in amounts sufficient to enable the enzymes to degrade the organism's capsule. The administered protein can be in pure form, a fragment of the peptide, or a modified form of the peptide retaining enzymatic activity. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine, and derivatives thereof. Alternative protein modification techniques may be used e.g., $NH_2$-acetylation or COOH-terminal amidation, to provide additional means for coupling or fusing the peptide to another protein or peptide molecule or to a support.

Pharmaceutically acceptable carriers include carriers that do not themselves induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, and inactive virus particles. The carrier can comprise, consist of, consist essentially of, or be a saline solution, dextrose, albumin, a serum, or any of those disclosed in U.S. Pub. Nos.: 2008/0138408; 2009/0061003; 2009/0123530; 2010/0303901; 2012/0034198; and 2016/0008290 and U.S. Pat. Nos. 6,992,066; 5,785,973; 7,485,294; 8,088,734; 8,753,645; 8,808,733; and 8,858,998.

The compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the compositions are prepared as injectables, either as liquid solutions or suspensions; solid forms suitable for solution in, or suspension in, liquid vehicles prior to injection may also be prepared. The preparation also may be emulsified or encapsulated in liposomes. Solutions for infusion or injection may be prepared in a conventional manner, e.g. with the addition of preservatives such as p-hydroxybenzoates or stabilizers such as alkali metal salts of ethylenediamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils and ethyl oleate are also useful herein.

In cases where intramuscular injection is the mode of administration, an isotonic formulation can be used. Generally, additives for isotonicity can include sodium chloride, dextrose, mannitol, sorbitol and lactose. In some cases isotonic solutions such as phosphate buffered saline are preferred. Stabilizers include glycerol, gelatin and albumin which may be included in the formulation. In some embodiments, a vasoconstriction agent is added to the formulation.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, polylactic acid or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions.

Administration of the compounds disclosed herein may be carried out by any suitable means, including parenteral injection (such as intravenous intraperitoneal, subcutaneous, or intramuscular injection), orally, or by topical application of the enzymes (typically carried in a pharmaceutical formulation) to an airway surface. Topical application to an airway surface can be carried out by intranasal administration (e.g., by use of dropper, swab, or inhaler which deposits a pharmaceutical formulation intranasally). Topical application to an airway surface can also be carried out by inhalation administration, such as by creating respirable particles of a pharmaceutical formulation (including both solid particles and liquid particles) containing the compounds as an aerosol suspension, and then causing the subject to inhale the respirable particles. Methods and apparatus for administering respirable particles of pharmaceutical formulations can be employed and include those disclosed in U.S. Pub. Nos.: 2006/0025326; 2010/0119587; and 2017/0314008; U.S. Pat. Nos. 6,017,528; 6,153,224; 6,221,338; 6,254,854; 6,893,635; 7,947,308; 8,137,657; and 9,249,424. Oral administration may be in the form of an ingestible liquid or solid formulation.

The treatment may be given to a subject in need of treatment and may include, but are not limited to, humans or ruminants, such as sheep and cows.

In order to accelerate treatment of the infection, the therapeutic agent may further include at least one complementary agent which can also potentiate the bactericidal activity of the enzyme. The complementary agent can be penicillin, ciprofloxacin, vancomycin, synthetic penicillins, bacitracin, methicillin, cephalosporin, polymyxin, cefaclor. Cefadroxil, cefamandole nafate, cefazolin, cefixime, cefmetazole, cefonioid, cefoperzone, ceforanide, cefotanme, cefotaxime, cefotetan, cefoxitin, cefpodoxime proxetil, ceftazidine, ceftizoxime, ceftriaxone, ceftriaxone moxalactam, cefuroxime, dihydratecephalothin, moxalactam, loracarbef, mafate, chelating agents, other antibiotics and any combinations thereof in amounts which are effective to synergistically enhance the therapeutic effect of the enzyme.

The treatment may be given in a single dose schedule, or a multiple dose schedule in which a primary course of treatment may be followed with a number of separate doses, followed by other doses given at subsequent time intervals required to maintain and or reinforce the response, for example, at 1-4 days for a second dose, and if needed, a subsequent dose(s) after several days. Separate doses may include separate routes of administration, for example, oral and inhaled, intraperitoneal and intravenous, etc. Examples of suitable treatment schedules include: (i) 0, 1 day and 7 days, (ii) 0 and 7 days, and (iii) 0 and 14 days, or other schedules sufficient to elicit the desired responses, reducing disease symptoms, or reduce severity of disease. A dosing schedule can be developed based on pharmacokinetic studies to maintain an effective blood level.

In some embodiments, the method comprises administering 5 µg/kg (weight of compound/body weight), 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, or 1000 mg/kg of pegylated, circularly permuted construct of the CapD enzyme in a single dose schedule, in total from a multiple dose schedule, or in each dose of a multiple dose schedule. In some embodiments, the method comprises administering 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of pegylated, circularly permuted construct of the CapD enzyme in a single dose schedule, in total from a multiple dose schedule, or in each dose of a multiple dose schedule. It is understood that higher doses could be administered for a localized administration and smaller doses could be administered systemically.

Kits may be useful for carrying out the present invention. In an embodiment, such kits comprise a first container holding enzymes as described herein. Kits can also comprise other containers holding solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The first container may be in secondary container, e.g. a box or a bag, along with other kit components.

Advantages

Unlike antibiotics, resistance to the enzyme treatment is unlikely to develop: this would require loss of the bacterial capsular material or damage to the capsule biosynthetic machinery. However, the capsular material is required for subversion of the host's immune responses. Thus, loss of the capsule would essentially produce the equivalent of a benign and non-virulent Sterne-like vaccine strain. If antibodies to CapD arise, these may not have negative effects in vivo. CapD is an enzyme naturally present in *B. anthracis* and is foreign to humans and animals, it is thought to be anchored to the bacterial membrane. Antibodies to this cell-surface protein would bind to the pathogen that is being cleared. During infection with encapsulated pathogenic encapsulated strains of *B. anthracis* the CapD enzyme is already present in the host. CapD shows evidence of product inhibition and the anchored enzyme in the bacteria is likely inhibited by the thick capsular material above it. The recombinant forms of CapD are being added to the exterior face of the encapsulated bacteria and can freely diffuse to avoid product inhibition, this leads to a net effect of unencapsulation.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A method of treating an infection of bacteria in a subject in need thereof, the method comprising:

administering a pegylated protein comprising SEQ ID NO: 2, SEQ ID NO: 3, SEQ ID NO: 4, or SEQ ID NO: 5 to the subject, wherein the bacteria has a capsule and is *Bacillus anthracis* or *Staphylococcus epidermidis*.

2. The method of claim 1, wherein the capsule comprises poly-γ-D-glutamic acid or poly-γ-DL-glutamic acid.

3. The method of claim 1, wherein the protein comprises SEQ ID NO: SEQ ID NO: 2, SEQ ID NO: 3, or SEQ ID NO: 4.

4. A method of treating anthrax in a subject in need thereof, the method comprising administering a pegylated protein comprising SEQ ID NO: 2, SEQ ID NO: 3, SEQ ID NO: 4, or SEQ ID NO: 5 to the subject.

5. The method of claim 4, wherein the protein comprises SEQ ID NO: SEQ ID NO: 2, SEQ ID NO: 3, or SEQ ID NO: 4.

* * * * *